United States Patent
Steinmetz

(10) Patent No.: US 11,253,610 B2
(45) Date of Patent: *Feb. 22, 2022

(54) PLANT VIRUS PARTICLES FOR DELIVERY OF ANTIMITOTIC AGENTS

(71) Applicant: CASE WESTERN RESERVE UNIVERSITY, Cleveland, OH (US)

(72) Inventor: Nicole F. Steinmetz, San Diego, CA (US)

(73) Assignee: CASE WESTERN RESERVE UNIVERSITY, Cleveland, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 17/030,793

(22) Filed: Sep. 24, 2020

(65) Prior Publication Data

US 2021/0008222 A1    Jan. 14, 2021

Related U.S. Application Data

(63) Continuation of application No. 16/688,561, filed on Nov. 19, 2019, now Pat. No. 10,874,747, which is a
(Continued)

(51) Int. Cl.
*A61K 47/69* (2017.01)
*C07K 5/062* (2006.01)
(Continued)

(52) U.S. Cl.
CPC ........ *A61K 47/6901* (2017.08); *A61K 31/401* (2013.01); *A61K 39/12* (2013.01);
(Continued)

(58) Field of Classification Search
None
See application file for complete search history.

(56) References Cited

U.S. PATENT DOCUMENTS 5,004,606 A    4/1991 Frincke
10,478,510 B2 * 11/2019 Steinmetz ............ A61K 31/401
(Continued)

FOREIGN PATENT DOCUMENTS

WO    2003092623 A2    11/2003
WO    2012078069 A1    6/2012
(Continued)

OTHER PUBLICATIONS

Applicant: Case Western Reserve University; "Cancer Immunotherapy Using Virus Particles"; European Patent Application No. 18764856.3 for Supplementary European Search Report dated Dec. 22, 2020; 8 pgs.
(Continued)

*Primary Examiner* — Shanon A. Foley
(74) *Attorney, Agent, or Firm* — Tarolli, Sundheim, Covell & Tummino LLP

(57) ABSTRACT

Anti-lymphoma plant virus particles are described. The anti-lymphoma plant virus particles include a filamentous or rod-shaped plant virus particle linked to an antimitotic agent. A therapeutically effective amount of an anti-lymphoma plant virus particle can be administered to a subject to provide a method of treating lymphoma.

19 Claims, 5 Drawing Sheets

Related U.S. Application Data continuation of application No. 15/745,358, filed as application No. PCT/US2016/042708 on Jul. 18, 2016, now Pat. No. 10,478,510.

(60) Provisional application No. 62/193,186, filed on Jul. 16, 2015.

(51) Int. Cl.
  *A61K 47/64* (2017.01)
  *A61K 47/68* (2017.01)
  *A61K 47/65* (2017.01)
  *A61P 35/00* (2006.01)
  *A61K 31/401* (2006.01)
  *A61K 39/12* (2006.01)

(52) U.S. Cl.
  CPC ............ *A61K 47/646* (2017.08); *A61K 47/65* (2017.08); *A61K 47/6811* (2017.08); *A61P 35/00* (2018.01); *C07K 5/06052* (2013.01)

(56) References Cited

U.S. PATENT DOCUMENTS

| | | | |
|---|---|---|---|
| 10,874,747 B2 * | 12/2020 | Steinmetz | .......... C07K 5/06052 |
| 2007/0258889 A1 | 11/2007 | Douglas | |

FOREIGN PATENT DOCUMENTS

| | | | |
|---|---|---|---|
| WO | 2013181557 A1 | 12/2013 | |
| WO | WO2013181557 | * | 12/2013 |

OTHER PUBLICATIONS

Lee, K. L., et al.; "Combination of Plant Virus Nanoparticle-Based in Situ Vaccination with Chemotherapy Potentiates Antitumor Response". Nano letters, 17(7); Epub Jun. 26, 2017; 4019-4028. https://doi.org/10.1021/acs.nanolett.7b00107.

Nicole F.Steinmetz; "Viral Nanoparticle Multimers"; U.S. Appl. No. 14/761,444, filed Jul. 16, 2015; Final Office Action dated Mar. 11, 2021; 11 pgs.

Nicole F.Steinmetz, et al.; "Coated Plant Virus Imaging Agents"; U.S. Appl. No. 16/279,482, filed Feb. 19, 2019; Non-Final Rejection dated Mar. 23, 2021; 91 pgs.

Inventor: Nicole Steinmetz, "Rod-Shaped Plant Virus Nanoparticles as Imaging Agent Platforms"; U.S. Appl. No. 16/149,828, filed Oct. 2, 2018, Office Action dated Aug. 28, 2020, 22 pgs.

Applicant: Case Western Reserve University; "Cancer Immunotherapy Using Virus Particles"; Office Action, dated Aug. 4, 2020; 3 pgs.

Applicant: Case Western Reserve University; "Plant Virus Particles for Delivery of Antimitotic Agents"; Extended European Search Report; dated Aug. 17, 2020; 11 pgs.

Canan Uluog, et al.: "Intermediate dose of methotrexate toxicity in non-Hodgkin lymphoma", General Pharmacology, vol. 32, 1999, pp. 215-218, XP55711259.

Trevor W. E. Robinson, et al., "The Journal of Investigative Dermatology the Effect of Methotrexate on Cell Division in the Epidermis of the Young Rat"; The Journal of investigative Dermatology, vol. 53, 1969, pp. 223-227, XP55711263.

Jantipa Jobsri, et al.: Plant Virus Particles Carrying Tumour Antigen Activate TLR7 and Induce High Levels of Protective Antibody, Plos One, vol. 10, No. 2, Jan. 1, 2015, pp. 1-16, XP055347065, DOI: 10.1371/journal.pone.0118096.

Pfizer Ltd.: "Package leaflet: Information for the patient", Jan. 1, 2014, XP55565400, Walton Oaks, Tadworth, Surrey, UK Retrieved from the Internet: URL:https://www.medicines.org.uk/emc/files/pil.6184.pdf [retrieved on Mar. 6, 2019].

Alaa A. Al. Aljabali, et al.; "CPMV-DOX Delivers", Molecular Pharmaceutics, vol. 10, No. 1, Jan. 7, 2013, pp. 3-10, XP055347068, US ISSN: 1543-8384, DOI: 10.1021/MP3002057.

Sourabh Shukla, et al.: "The Impact of Aspect Ratio on the Biodistribution and Tumor Homing of Rigid Soft-Matter Nanorods", Advanced Healthcare Materials, vol. 4, No. 6, Apr. 1, 2015, pp. 874-882, XP055473103, DE ISSN: 2192-2640, DOI: 10.1002/adhm.201400641.

Francisco, Joseph A., et al.; "cAC10-vcMMAE, an anti-CD30-monomethyl auristatin E conjugate with potent and selective antitumor activity", Blood, American Society of Hematology, US, vol. 102, No. 4, Aug. 15, 2003, pp. 1458-1465, XP002738948, ISSN: 0006-4971, DOI: 10.1182/BLOOD-2003-01-0039.

\* cited by examiner

Fig. 3A
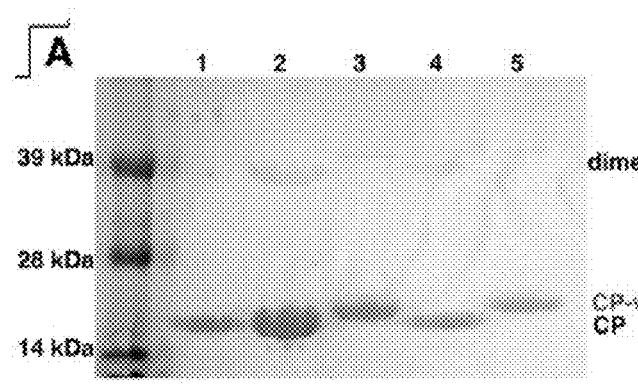
Fig. 3B
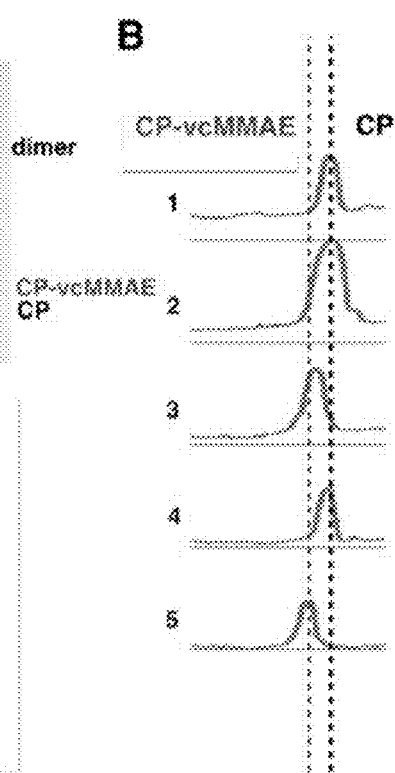
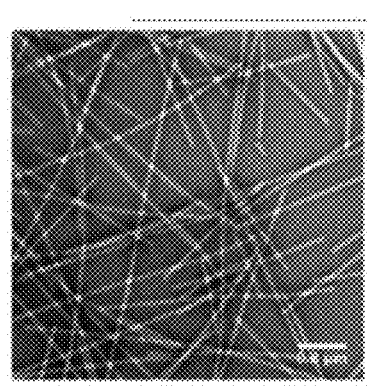
Fig. 3C

PLANT VIRUS PARTICLES FOR DELIVERY OF ANTIMITOTIC AGENTS

CROSS-REFERENCE TO RELATED APPLICATIONS

This application claims priority to U.S. Provisional Application Ser. No. 62/193,186, filed on Jul. 16, 2015, the disclosure of which is hereby incorporated by reference in its entirety.

BACKGROUND

Lymphoma can be divided into two categories: Hodgkin's lymphoma, and Non-Hodgkin's lymphoma. Hodgkin's disease is a specific kind of lymphoma commonly diagnosed by the appearance of Reed-Sternberg cells in tissue biopsies. Fortunately, Hodgkin's lymphoma is one of the most curable forms of cancer, and patients with this disease have a 5-year survival rate of 85%. However, Non-Hodgkin's lymphoma is the more common type of lymphoma, and covers a range of lymphatic cancers, including: diffuse large B-cell lymphoma, follicular lymphoma, small lymphocytic lymphoma, mantle cell lymphoma, marginal zone B-cell lymphoma, burkitt lymphoma, lymphoplasmacytic lymphoma, hairy cell leukemia, primary central nervous system lymphoma, precursor T-lymphoblastic lymphoma and peripheral T-cell lymphomas.

The most common form of non-Hodgkin's lymphoma is diffuse large B-cell lymphoma. Patients with this disease have poor survival with a 5 year survival rate as low as 58%. The treatment success rates and prognosis heavily depend on the stage at which the disease is diagnosed. Both, Hodgkin's and non-Hodgkin's lymphoma are staged according to the Ann Arbor staging system, which stages a cancer from I to IV. The number represents the extent to which the cancer has spread, with stages I-III representing one to three cancerous lymph nodes, respectively. Stage IV marks disseminated disease that has spread into secondary organs away from the main sites of disease. Depending on the disease staging at the time of diagnoses, the treatment regime differs: For example, for patients with non-Hodgkin's lymphoma stage I/II, the clinical protocol calls for a combination therapy of Rituximab, cyclophosphamide, vincristine, doxorubicin, and prednisone (R-CHOP) for 3-4 cycles. In the advanced stages III and IV, R—CHOP is administered for 6 cycles, sometimes with involved-field radiation therapy (IFRT). In cases of relapse, the patient may be administered platinum based chemotherapy, radio-immunotherapy, and higher doses of previous chemotherapeutics. Chen et al., Expert Opin. Drug Deliv., vol. 2, no. 5, pp. 873-890 (2005).

It is clear that novel and innovative therapeutic strategies are needed to increase the survival rates as well as to mitigate the adverse side effects associated with many of the treatment regimes described above. Key strategies include to device methods to lower the effective dose of systemically administered toxic drugs—this can be achieved through targeted drug delivery strategies thereby increasing the partitioning of the drug to the site of the disease.

One avenue of disease-specific drug targeting is found in the application of antibodies, and more specifically antibody-drug conjugates (ADCs). Bouchard et al., Bioorg. Med. Chem. Lett., vol. 24, no. 23, pp. 5357-5363 (2014). Antibodies can be selected to virtually any disease target; the antibody itself can be therapeutic or can carry a therapeutic cargo. Drug-targeting my means of antibody target-antigen specificity holds great potential for cancer therapy. Tumor neoantigens have been discovered allowing the selection of target-specific antibodies, therefore allowing drug targeting Immunotherapies are gaining momentum not only in clinical trials, but such biological therapies have become a clinical reality. A notable example is the monoclonal antibodies therapy rituximab. Rituximab targets CD20, which is a protein expressed on most non-Hodgkin's B-cell lymphoma. The CD20 target is not normally found in circulation, therefore making this therapy highly specific. Rituximab is the standard for patients diagnosed with non-Hodgkin's B-cell lymphoma, yet the survival rates are only 58%, indicating there is still room for improvement. Feugier et al., J. Clin. Oncol. Off. J. Am. Soc. Clin. Oncol., vol. 23, no. 18, pp. 4117-4126 (2005).

Another avenue toward targeted therapies is the development of nanoparticles. Nanoparticles typically measure between 10-500 nm and are thus small enough to efficiently navigate circulation, traffic through tissues and target and enter cells. Albanese et al., Annu. Rev. Biomed. Eng., vol. 14, no. 1, pp. 1-16 (2012); Yildiz et al., Curr. Opin. Biotechnol., vol. 22, no. 6, pp. 901-908 (2011). Nanoparticles are larger than antibodies and offer multivalency; i.e., while an IgG antibody offers two binding sites for antigen binding, a nanoparticle has the potential to bind to multiple hundred-to-thousands of binding sites. The multivalency provides a mechanism to increase target specificity through added avidity effects. Furthermore, multifunctional designs are possible, where toxic payloads and/or contrast agents are loaded into the nanoparticle while targeting ligands enable tissue-specific delivery with increased payload delivery. M. Wu and Z. Niu, Nanoparticles for Biotherapeutic Delivery (Volume 1), Future Science Ltd, pp. 50-62 (2015); Xiao et al., Cancer Res., vol. 72, no. 8, pp. 2100-2110, (2012).

Nanoparticles take advantage of their size and shape to gain increased uptake into tumor vasculature. Rapid angiogenesis occurs to supply the tumor with nutrients and oxygen and support the increased growth—as a result the neovasculature is leaky with a porous endothelium. This leaky vasculature with pores at the nano-to-micron size, create the perfect entry ways for nanoparticles to enter the tumor. Wong et al., PLoS ONE, vol. 10, no. 5, (2015) Simultaneously, the microenvironment created by the angiogenesis causes local compressive forces, which in turn lead to poor lymphatic drainage. This effect is known as the enhanced permeability and retention effect (EPR). Simply by flowing through the bloodstream, the nanoparticles are likely to extravasate into the tumor, and stay in that environment due to the EPR effect. Some nanoparticles, such as doxil, a liposomal formulation of doxorubicin, have been clinically approved for treatments in ovarian cancer, AIDS-related Kaposi sarcoma, and multiple myeloma. Nevertheless, while the research development pipeline is moving rapidly, nanoparticle therapies have not yet made it into the standard of care for non-Hodgkin's-lymphoma. Rink et al., Curr. Opin. Oncol., vol. 25, no. 6, pp. 646-651 (2013). Of course, the EPR effect does not hold count for blood cancers such as non-Hodgkin's-lymphoma. Alternative methods must be developed to target potent therapies to this disease.

SUMMARY

Nanoparticle drug therapies have shown great promise enabling drug delivery to sites of disease based on their size, shape and surface engineerability. Viral nanoparticles are biology-derived carriers that are growing in popularity due to their simple genetic and chemical modification, size tunability from spherical to high-aspect ratio, and biocompatibility. These attributes give a wide range of tools for engineers to design therapeutics with specific toxic loads and surface chemistries to efficiently navigate the body. The inventors have developed a viral nanoparticle using the nucleoprotein component from the tobacco mosaic virus (TMV) as the carrier for delivery of the antimitotic drug valine-citrulline monomethyl auristatin E (vcMMAE). In addition, they have demonstrated successful synthesis of the formulation, and the effective cell killing of Non-Hodgkin's lymphoma in vitro.

Accordingly, in one aspect, the present invention provides an anti-lymphoma virus particle, comprising a filamentous or rod-shaped plant virus particle linked to an antimitotic agent. In some embodiments, the plant virus particle is a tobacco mosaic virus, while in other embodiments the antimitotic agent monomethyl auristatin E (MMAE).

In another aspect, the present invention provides a method of treating lymphoma in a subject by administering to the subject a therapeutically effective amount of an anti-lymphoma virus particle, comprising a filamentous or rod-shaped plant virus particle linked to an antimitotic agent. In some embodiments, the lymphoma is non-Hodgkin's lymphoma, while in further embodiments the anti-lymphoma virus particle is administered together with a pharmaceutically acceptable carrier.

BRIEF DESCRIPTION OF THE FIGURES

The present invention may be more readily understood by reference to the following drawings.

FIG. 3A and FIG. 3B and FIG. 3C provide graphs and images showing the biochemical characterization of the vcMMAE-loaded TMV. A) SDS-gel: lanes Lane 1) TMV-lys, Lanes 2 and 4) TMV-SATP, Lanes 3 and 5) TMV-vcMMAE. B) Densinometric analysis showing two distinct bands; CP vs CP-vcMMAE. C) Transmission electron microscopy (TEM) of negatively-stained TMV-vcMMAE.

DETAILED DESCRIPTION

Figure 1A:
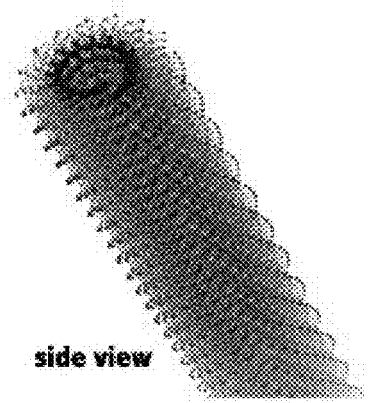
FIG. 1A and FIG. 1B provide images showing the structure of tobacco mosaic virus (TMV). Chimera image shows the 300 nm by 18 nm rod with top view (1A) and side view (1B). Coat protein subunit in lower right highlights the reactive groups, glutamines on the interior, and lysine on the exterior.

The present invention provides anti-lymphoma plant virus particles that are a filamentous or rod-shaped plant virus particle linked to an antimitotic agent. In an additional aspect of the invention, a therapeutically effective amount of an anti-lymphoma plant virus particle is administered to a subject to provide a method of treating lymphoma.

Definitions

It is to be understood that this invention is not limited to particular methods, reagents, compounds, compositions or biological systems, which can, of course, vary. It is also to be understood that the terminology used herein is for the purpose of describing particular embodiments only, and is not intended to be limiting. As used in this specification and the appended claims, the singular forms "a", "an" and "the" include plural references unless the content clearly dictates otherwise. Thus, for example, reference to "a virus particle" includes a combination of two or more virus particles, and the like.

The term "about" as used herein when referring to a measurable value such as an amount, a temporal duration, and the like, is meant to encompass variations of ±20% or 110%, more preferably ±5%, even more preferably ±1%, and still more preferably ±0.1% from the specified value, as such variations are appropriate to perform the disclosed methods.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

"Treat", "treating", and "treatment", etc., as used herein, refer to any action providing a benefit to a subject afflicted with a condition or disease such as lymphoma, including improvement in the condition through lessening or suppression of at least one symptom, delay in progression of the disease, etc.

Prevention, as used herein, refers to any action providing a benefit to a subject at risk of being afflicted with a condition or disease such as lymphoma, including avoidance of the development of lymphoma or a decrease of one or more symptoms of the disease should lymphoma develop. The subject may be at risk due to exposure to a carcinogen, or as a result of family history.

A "subject," as used herein, can be any animal, and may also be referred to as the patient. Preferably the subject is a vertebrate animal, and more preferably the subject is a mammal, such as a domesticated farm animal (e.g., cow, horse, pig) or pet (e.g., dog, cat). In some embodiments, the subject is a human.

"Pharmaceutically acceptable" as used herein means that the compound or composition is suitable for administration to a subject for the methods described herein, without unduly deleterious side effects in light of the severity of the disease and necessity of the treatment.

The terms "therapeutically effective" and "pharmacologically effective" are intended to qualify the amount of each agent which will achieve the goal of decreasing disease severity while avoiding adverse side effects such as those typically associated with alternative therapies. The therapeutically effective amount may be administered in one or more doses.

"Targeting," as used herein, refers to the ability of filamentous or rod shaped plant virus particles to be delivered to and preferentially accumulate in cancer tissue in a subject.

In one aspect, the invention provides an anti-lymphoma virus particle, comprising a filamentous or rod-shaped plant virus particle linked to an antimitotic agent. Providing anti-lymphoma plant virus particle with an anti-mitotic agent linked to the plant virus particle helps protect the anti-mitotic agents from degrading or having toxic effects in the bloodstream, while allowing their release upon degradation of the virus particles within lymphoma cells.

Filamentous and Rod-Shaped Plant Viruses

A filamentous plant virus is a virus that primarily infects plants and has a non-enveloped filamentous structure. A filamentous structure is a long, thin virion that has a filament-like or rod-like shape that is much longer than it is wide and therefore has a high-aspect ratio. For example, Alphaflexiviridae have a length of about 470 to about 800 nm, and a diameter of about 12-13 nm. Filament-like virus particles are flexible in addition to being long and thin, and therefore some embodiments of the invention are directed to use of a flexible filamentous plant virus.

In some embodiments, the filamentous plant virus belongs to a specific virus family, genus, or species. For example, in some embodiments, the filamentous plant virus belongs to the Alphaflexiviridae family. The Alphaflexiviridae family includes the genus *Allexivirus, Botrexvirus, Lolavirus, Mandarivirus, Potexvirus*, and *Sclerodamavirus*. In some embodiments, the filamentous plant virus belongs to the genus *Potexvirus*. In further embodiments, the filamentous plant virus belongs to the Potato Virus X species.

A rod-shaped plant virus is a virus that primarily infects plants, is non-enveloped, and is shaped as a rigid helical rod with a helical symmetry. Rod shaped viruses also include a central canal. Rod-shaped plant virus particles are distinguished from filamentous plant virus particles as a result of being inflexible, shorter, and thicker in diameter. For example, Virgaviridae have a length of about 200 to about 400 nm, and a diameter of about 15-25 nm. Virgaviridae have other characteristics, such as having a single-stranded RNA positive sense genome with a 3'-tRNA like structure and no polyA tail, and coat proteins of 19-24 kilodaltons.

In some embodiments, the rod-shaped plant virus belongs to a specific virus family, genus, or species. For example, in some embodiments, the rod-shaped plant virus belongs to the Virgaviridae family. The Virgaviridae family includes the genus *Furovirus, Hordevirus, Pecluvirus, Pomovirus, Tobamovirus*, and *Tobravirus*. In some embodiments, the rod-shaped plant virus belongs to the genus *Tobamovirus*. In further embodiments, the rod-shaped plant virus belongs to the tobacco mosaic virus species. The tobacco mosaic virus has a capsid made from 2130 molecules of coat protein and one molecule of genomic single strand RNA 6400 bases long. The coat protein self-assembles into the rod like helical structure (16.3 proteins per helix turn) around the RNA which forms a hairpin loop structure. The protein monomer consists of 158 amino acids which are assembled into four main alpha-helices, which are joined by a prominent loop proximal to the axis of the virion. Virions are ~300 nm in length and ~18 nm in diameter. Negatively stained electron microphotographs show a distinct inner channel of ~4 nm.

Filamentous and rod-shaped plant virus particles have an interior and an exterior. The exterior of a plant virus particle is the portion of the virus particle that is directly exposed to the environment. The interior of the plant virus particle is the portion of the virus particle that typically is adjacent to the genomic material within the virus particle, and is not directly exposed to the environment. In some embodiments, the plant virus particles are genetically modified to have one or more additional attachment sites on the interior or exterior of the plant virus particle. For example, the interior or exterior of the plant virus particle can be modified to include one or more additional lysine residues.

Antimitotic Compounds

Antimitotic compounds are drugs that inhibit mitosis, or cell division, and typically function by disrupt microtubules, which are structures that pull cells apart during cell division. Antimitotic compounds are useful for treating lymphoma because cancer cells are able to grow and eventually spread through the body (metastasize) through continuous mitotic division, and are therefore more sensitive to inhibition of mitosis than normal cells.

There are a wide variety of known antimitotic compounds which can be linked to plant virus particles according to the present invention. Classes of antimitotic compounds include taxanes, vinca alkaloids, and dolastatins. Examples of taxanes include paclitaxel and docetaxel, while examples of vinca alkaloids include vinblastine, vincristine, vindesine, and venorelbine. Dolastatins are compounds identified in the extracts of the sea hare *Dolabella auricularia* that have shown pronounced antineoplastic and antimitotic activity. Examples of dolastatins include dolastatin 10, dolastatin 11, dolastatin 15, and monomethyl auristatin E (MMAE), which is a dolastatin 10 derivative. A further dolastatin is dolastatin is valine-citrulline monomethyl auristatin E (vcMMAE), which is an analog of MMAE that has been modified to facilitate easy attachment to proteins such as antibodies. Other examples of antimitotic compounds include colchicine, podophyllotoxin, and glaziovianin A.

Association of Antimitotic Agents with the Plant Virus Particles

The present invention provides an anti-lymphoma virus particle, comprising a filamentous or rod-shaped plant virus particle linked to an antimitotic agent. The antimitotic agent can be linked to either the interior of the plant virus particle, the exterior of the plant virus particle, or to both the interior and exterior of the plant virus particle. An antimitotic agent is linked to the plant virus particle by being chemical bonded to the plant virus particle, though the linkage can be either direct or indirect, where indirect linkage is through an intermediate linking molecule.

In general, antimitotic agents can be conjugated to the filamentous or rod-shaped plant virus particles by any suitable technique, with appropriate consideration of the need for pharmacokinetic stability and reduced overall toxicity to the patient. The term "conjugating" when made in reference to an antimitotic agent and a plant virus particle as used herein means covalently linking the agent to the virus subject to the single limitation that the nature and size of the agent and the site at which it is covalently linked to the virus particle do not interfere with the biodistribution of the modified virus.

An agent can be coupled to a filamentous or rod-shaped plant virus particle either directly or indirectly (e.g. via a linker group). In some embodiments, the agent is directly attached to a functional group capable of reacting with the agent. For example, viral coat proteins include lysines that have a free amino group that can be capable of reacting with a carbonyl-containing group, such as an anhydride or an acid halide, or with an alkyl group containing a good leaving group (e.g., a halide). Viral coat proteins also contain glutamic and aspartic acids. The carboxylate groups of these amino acids also present attractive targets for functionalization using carbodiimide activated linker molecules; cysteines can also be present which facilitate chemical coupling via thiol-selective chemistry (e.g., maleimide-activated compounds). In addition, genetic modification can be applied to introduce any desired functional residue, including non-natural amino acids, e.g. alkyne- or azide-functional groups. See Pokorski, J. K. and N. F. Steinmetz Mol Pharm 8(1): 29-43 (2011).

Alternatively, a suitable chemical linker group can be used. A linker group can serve to increase the chemical reactivity of a substituent on either the agent or the virus particle, and thus increase the coupling efficiency. Preferred groups suitable for attaching agents to virus particles are lysine residues present in the viral coat protein. Suitable linkage chemistries include maleimidyl linkers and alkyl halide linkers and succinimidyl (e.g., N-hydroxysuccinimidyl (NHS)) linkers (which react with a primary amine on the filamentous or rod-shaped plant virus particle). Several primary amine and sulfhydryl groups are present on viral coat proteins, and additional groups can be designed into recombinant viral coat proteins. It will be evident to those skilled in the art that a variety of bifunctional or polyfunctional reagents, both homo- and hetero-functional, can be employed as a linker group. Coupling can be affected, for example, through amino groups, carboxyl groups, sulfhydryl groups or oxidized carbohydrate residues.

In some embodiments, for example where an antimitotic agent is more potent when free from the plant virus particle of the present invention, it can be desirable to use a linker group which is cleavable during or upon internalization into a cell, or which is gradually cleavable over time in the extracellular environment. A number of different cleavable linker groups have been described. The mechanisms for the intracellular release of a cytotoxic moiety agent from these linker groups include cleavage by reduction of a disulfide bond (e.g., U.S. Pat. No. 4,489,710); by irradiation of a photolabile bond (e.g., U.S. Pat. No. 4,625,014); by hydrolysis of derivatized amino acid side chains (e.g., U.S. Pat. No. 4,638,045); by serum complement-mediated hydrolysis (e.g., U.S. Pat. No. 4,671,958); and acid-catalyzed hydrolysis (e.g., U.S. Pat. No. 4,569,789).

It can be desirable to couple more than one type of antimitotic agent within a filamentous or rod-shaped plant virus particle of the invention. By poly-derivatizing the plant viral particle of the invention, several cytotoxic strategies can be simultaneously implemented. For example, more than one type of anti-mitotic agent can be coupled to a filamentous or rod-shaped plant virus particle.

Lymphoma Treatment

In one aspect, the present invention provides a method of treating lymphoma in a subject by administering to the subject a therapeutically effective amount of an anti-lymphoma virus particle. The anti-lymphoma virus particle can have any of the features described herein. For example, the plant virus particles can be tobacco mosaic virus particles, and in some embodiments MMAE-based antimitotic agents can be used.

Filamentous or rod-shaped plant virus particles including antimitotic agents can be used to treat lymphoma, which is a type of cancer. "Cancer" refers to any of a number of diseases that are characterized by uncontrolled, abnormal proliferation of cells, the ability of affected cells to spread locally or through the bloodstream and lymphatic system to other parts of the body (i.e., metastasize) as well as any of a number of characteristic structural and/or molecular features. A "cancer cell" refers to a cell undergoing early, intermediate or advanced stages of multi-step neoplastic progression. The features of early, intermediate and advanced stages of neoplastic progression have been described using microscopy. Cancer cells at each of the three stages of neoplastic progression generally have abnormal karyotypes, including translocations, inversion, deletions, isochromosomes, monosomies, and extra chromosomes. Cancer cells include "hyperplastic cells," that is, cells in the early stages of malignant progression, "dysplastic cells," that is, cells in the intermediate stages of neoplastic progression, and "neoplastic cells," that is, cells in the advanced stages of neoplastic progression.

Lymphoma is a group of blood cell tumors that develop from lymphatic cells. The two main categories of lymphomas are Hodgkin lymphomas and the non-Hodgkin lymphomas (NHL). About 90% of lymphomas are non-Hodgkin lymphomas. Examples of non-Hodgkin's lymphoma include diffuse large B-cell lymphoma, follicular lymphoma, small lymphocytic lymphoma, mantle cell lymphoma, marginal zone B-cell lymphoma, burkitt lymphoma, lymphoplasmacytic lymphoma, hairy cell leukemia, primary central nervous system lymphoma, precursor T-lymphoblastic lymphoma and peripheral T-cell lymphomas. The most common type of lymphoma is B-cell lymphoma. Examples of non-Hodgkin's B-cell lymphoma include diffuse large B-cell lymphoma, follicular lymphoma, marginal zone B-cell lymphoma or mucosa-associated lymphatic tissue lymphoma, small lymphocytic lymphoma (also known as chronic lymphocytic leukemia), and mantle cell lymphoma (MCL). Additional, more rare forms of B-cell lymphoma include Burkitt's lymphoma, lymphoplasmacytic lymphoma, nodal marginal zone B cell lymphoma, splenic marginal zone lymphoma, intravascular large B-cell lymphoma, primary effusion lymphoma, lymphomatoid granulomatosis, primary central nervous system lymphoma, ALK-positive large B-cell lymphoma, plasmablastic lymphoma, and large B-cell lymphoma arising in HHV8-associated multicentric Castleman's disease.

The filamentous or rod-shaped plant virus is used to target lymphoma in a subject. As used herein, targeting cancer tissue includes the ability of the anti-lymphoma virus particles to reach and preferably accumulate in lymphoma after being administered to the subject. The ability of filamentous or rod-shaped plant virus particles to target cancer tissue is supported by the biodistribution studies carried out by the inventors. See International Patent Publication WO/2013/181557, the disclosure of which is incorporated herein by reference. While not intending to be bound by theory, it currently appears that filamentous and rod-shaped plant virus particles are drawn to the leaky vasculature caused by the angiogenesis associated with rapid tumor growth, and this leaky vasculature encourages entry for nanoparticles through small pores, thereby delivering the anti-lymphoma plant virus particles to the lymphoma cells. As a result of this preferential accumulation, embodiments of the invention can deliver about 10%, about 20%, about 30%, about 40%, or even about 50% or more of the injected dose to tumor tissue.

In some embodiments, the subject being administered a therapeutically effective amount of an anti-lymphoma plant virus particle is a subject who has been identified as having lymphoma. As is known to those skilled in the art, there are a variety of methods of identifying (i.e., diagnosing) a subject who has lymphoma. Symptoms of lymphoma include lymphadenopathy or swelling of lymph nodes, which is the primary presentation in lymphoma. Additional, systemic symptoms associated with both Hodgkin lymphoma and non-Hodgkin lymphoma include fever, night sweats, and weight loss. Lymphoma is definitively diagnosed by a lymph node biopsy, meaning a partial or total excision of a lymph node examined under the microscope, which reveals histopathological features that may indicate lymphoma. After lymphoma is diagnosed, a variety of tests may be carried out to look for specific features characteristic of different types of lymphoma. These tests include: immunophenotyping, flow cytometry, and fluorescence in situ hybridization testing.

In some embodiments, the method further includes the step of ablating the lymphoma. Ablating the lymphoma can be accomplished using a method selected from the group consisting of cryoablation, thermal ablation, radiotherapy, chemotherapy, radiofrequency ablation, electroporation, alcohol ablation, high intensity focused ultrasound, photodynamic therapy, administration of monoclonal antibodies, and administration of immunotoxins.

In some embodiments, the step ablating the lymphoma includes administering a therapeutically effective amount of an anticancer agent commonly used to treat lymphoma to the subject. Examples of anticancer agents commonly used to treat lymphoma include alkylating agents such as cyclophosphamide (Cytoxan®), chlorambucil, bendamustine (Treanda®), and ifosfamide (Ifex®); Corticosteroids, such as prednisone and dexamethasone (Decadron®); platinum-based drugs such as cisplatin, carboplatin, and oxaliplatin; purine analogs such as fludarabine (Fludara®), pentostatin (Nipent®), and cladribine (2-CdA, Leustatin®); anti-metabolites such as cytarabine (ara-C), gemcitabine (Gemzar®), methotrexate, and pralatrexate (Folotyn®); and various other compounds such as vincristine (Oncovin®), doxorubicin (Adriamycin®), mitoxantrone, etoposide (VP-16), and bleomycin.

Targeting Moieties

In some embodiments, a targeting moiety can also be attached to the filamentous or rod-shaped plant virus particle. By "targeting moiety" herein is meant a functional group which serves to target or direct the virus particle to a particular location, cell type, diseased tissue, or association. In general, the targeting moiety is directed against a target molecule. Thus, for example, antibodies, cell surface receptor ligands and hormones, lipids, sugars and dextrans, alcohols, bile acids, fatty acids, amino acids, peptides and nucleic acids may all be attached to localize or target the anti-lymphoma plant virus particle to a particular site. In some embodiments, the targeting moiety allows targeting of the plant virus particles of the invention to a particular tissue or the surface of a cell. Preferably, the targeting moiety is linked to the exterior surface of the virus to provide easier access to the target molecule.

In some embodiments, the targeting moiety is a peptide. In further embodiments, the targeting moiety is an antibody. The term "antibody" includes antibody fragments, as are known in the art, including Fab Fab$_2$, single chain antibodies (Fv for example), chimeric antibodies, etc., either produced by the modification of whole antibodies or those synthesized de novo using recombinant DNA technologies. In further embodiments, the antibody targeting moieties of the invention are humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin.

In some embodiments, the antibody is directed against a cell-surface marker on a cancer cell; that is, the target molecule is a cell surface molecule. As is known in the art, there are a wide variety of cell surface molecules known to be differentially expressed on tumor cells, including, but not limited to, HER2. Examples of physiologically relevant carbohydrates may be used as cell-surface markers include, but are not limited to, antibodies against markers for breast cancer (CA 15-3, CA 549, CA 27.29), mucin-like carcinoma associated antigen (MCA), ovarian cancer (CA125), pancreatic cancer (DE-PAN-2), and colorectal and pancreatic cancer (CA 19, CA 50, CA242). In some embodiments, a cell surface molecule known to be differentially expressed on lymphoma cells is used. Examples of such cell surface markers include CD20, CD22, and CD40.

Coatings on the Virus Particle Exterior

In some embodiments, a coating can be added to the exterior of the plant virus particle to improve bioavailability. Administering plant virus particles to a subject can sometimes generate an immune response. An "immune response" refers to the concerted action of lymphocytes, antigen presenting cells, phagocytic cells, granulocytes, and soluble macromolecules produced by the above cells or the liver (including antibodies, cytokines, and complement) that results in selective damage to, destruction of, or elimination from the human body of cancerous cells, metastatic tumor cells, invading pathogens, cells or tissues infected with pathogens, or, in cases of autoimmunity or pathological inflammation, normal human cells or tissues. Components of an immune response can be detected in vitro by various methods that are well known to those of ordinary skill in the art.

Generation of an immune response by the anti-lymphoma virus particles is typically undesirable. Accordingly, in some embodiments it may be preferable to modify the exterior of the plant virus particle or take other steps to decrease the immune response. For example, an immunosuppressant compound can be administered to decrease the immune response. More preferably, the anti-lymphoma virus particle can be modified to decrease its immunogenicity. Examples of methods suitable for decreasing immunity include attachment of anti-fouling (e.g., zwitterionic) polymers, glycosylation of the virus carrier, and PEGylation.

In some embodiments, the immunogenicity of the anti-lymphoma virus particle is decreased by PEGylation. PEGylation is the process of covalent attachment of polyethylene glycol (PEG) polymer chains to a molecule such as a filamentous plant virus carrier. PEGylation can be achieved by incubation of a reactive derivative of PEG with the plant virus particle exterior. The covalent attachment of PEG to the anti-lymphoma virus particle can "mask" the agent from the host's immune system, and reduce production of antibodies against the carrier. PEGylation also may provide other benefits. PEGylation can be used to vary the circulation time of the filamentous plant virus carrier. For example, use of PEG 5,000 can provide an anti-lymphoma virus particle with a circulation half-life of about 12.5 minutes, while use of PEG 20,000 can provide an anti-lymphoma virus particle with a circulation half life of about 110 minutes.

The first step of PEGylation is providing suitable functionalization of the PEG polymer at one or both terminal positions of the polymer. The chemically active or activated derivatives of the PEG polymer are prepared to attach the PEG to the anti-lymphoma virus particle. There are generally two methods that can be used to carry out PEGylation; a solution phase batch process and an on-column fed-batch process. The simple and commonly adopted batch process involves the mixing of reagents together in a suitable buffer solution, preferably at a temperature between 4 and 6° C., followed by the separation and purification of the desired product using a chromatographic technique.

Administration and Formulation of Anti-Lymphoma Plant Virus Particles

In some embodiments, the anti-lymphoma virus particle is administered together with a pharmaceutically acceptable carrier to provide a pharmaceutical formulation. Pharmaceutically acceptable carriers enable the anti-lymphoma virus particle to be delivered to the subject in an effective manner while minimizing side effects, and can include a variety of diluents or excipients known to those of ordinary skill in the art. Formulations include, but are not limited to, those suitable for oral, rectal, vaginal, topical, nasal, ophthalmic, or parental (including subcutaneous, intramuscular, intraperitoneal, intratumoral, and intravenous) administration. For example, for parenteral administration, isotonic saline is preferred. For topical administration, a cream, including a carrier such as dimethylsulfoxide (DMSO), or other agents typically found in topical creams that do not block or inhibit activity of the compound, can be used. Other suitable carriers include, but are not limited to, alcohol, phosphate buffered saline, and other balanced salt solutions.

The formulations may be conveniently presented in unit dosage form and may be prepared by any of the methods well known in the art of pharmacy. Preferably, such methods include the step of bringing the anti-lymphoma virus particle into association with a pharmaceutically acceptable carrier that constitutes one or more accessory ingredients. In general, the formulations are prepared by uniformly and intimately bringing the anti-lymphoma virus particle into association with a liquid carrier, a finely divided solid carrier, or both, and then, if necessary, shaping the product into the desired formulations. The methods of the invention include administering to a subject, preferably a mammal, and more preferably a human, the composition of the invention in an amount effective to produce the desired effect. The formulated anti-lymphoma virus particle can be administered as a single dose or in multiple doses.

Useful dosages of the antimitotic agents and anti-lymphoma virus particles can be determined by comparing their in vitro activity and the in vivo activity in animal models. Methods for extrapolation of effective dosages in mice, and other animals, to humans are known in the art; for example, see U.S. Pat. No. 4,938,949. An amount adequate to accomplish therapeutic or prophylactic treatment is defined as a therapeutically- or prophylactically-effective dose. In both prophylactic and therapeutic regimes, agents are usually administered in several dosages until an effect has been achieved. Effective doses of the anti-lymphoma virus particles vary depending upon many different factors, including means of administration, target site, physiological state of the patient, whether the patient is human or an animal, other medications administered, and whether treatment is prophylactic or therapeutic.

For administration of the anti-lymphoma virus particles for treatment of lymphoma in a subject, the dosage of the antic-mitotic agent ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. A suitable amount of anti-lymphoma virus particle is used to provide the desired dosage. An exemplary treatment regime entails administration once per every two weeks or once a month or once every 3 to 6 months. The anti-lymphoma virus particle is usually administered on multiple occasions. Alternatively, the anti-lymphoma virus particle can be administered as a sustained release formulation, in which case less frequent administration is required. In therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes).

For parenteral administration, compositions of the invention can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions.

The present invention is illustrated by the following example. It is to be understood that the particular example, materials, amounts, and procedures are to be interpreted broadly in accordance with the scope and spirit of the invention as set forth herein.

EXAMPLE

Figure 1B:
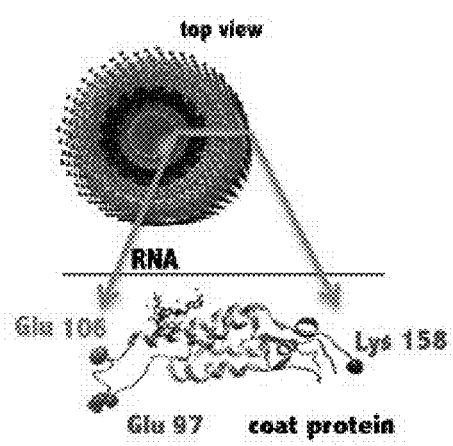

Example 1: Delivery of Potent Anti-Mitotic Chemotherapeutic Using High Aspect Ratio, Soft Matter Nanoparticles A study of the development and testing of an anti-mitotic soft matter virus-based nanoparticle (VNP) using the nucleoprotein components of the tobacco mosaic virus (TMV, FIG. 1) is described. TMV is a plant virus that has several properties that it a favorable nanoparticle choice for biomedical applications. TMV offers a stable, monodisperse, and biocompatible protein-based scaffold. J. K. Pokorski and N. F. Steinmetz, Mol. Pharm., vol. 8, no. 1, pp. 29-43 (2011); Wen et al., J. Vis. Exp. JoVE, no. 69 (2012). The TMV structure is known to an atomic resolution, this allows the biomedical engineer and chemist to identify specific reactive groups to be targeted for bioconjugation of medical cargo such as drug or contrast agents and display of targeting ligands or shielding molecules. To be specific, TMV is a 300 nm by 18 nm rigid hollow nanotube with a 4 nm-wide interior channel (see FIG. 1). The rod shaped, soft matter nanoparticle consists of 2130 identical coat proteins. The reactive groups on the exterior or interior channel are known: with tyrosine 139 on the exterior, and glutamine 97 and glutamine 106 on the interior. Furthermore, genetic engineering, allows the introduction of new functionality. One example of this is the lysine-added mutant 'TMV-lysine' that displays reactive lysine groups on the exterior protein shell, and is easily modifiable using well known N-Hydroxysuccinimide (NHS) chemistry (TMV-lys, FIG. 1). To conclude, TMV offers a modifiable, uniform, and organic nanoparticle scaffold to build a therapeutic nanoformulation.

In a previous study, the inventors observed that TMV was taken up by the cervical cancer cell line HeLa; uptake was by endocytosis targeting the TMV-based nanoparticle into the endolysosomal compartment. In this low pH environment with highly reactive protease and hydrolase, the particles were left intact over the time course studied (1 week), but the chemically bio-conjugated molecules on the exterior and interior were rapidly cleaved. Wen et al., Bioconjug. Chem., vol. 26, no. 1, pp. 51-62 (2015). Based on these previous findings, the inventors hypothesized that they could make use of the natural cancer cell uptake and fate of the TMV carrier to deliver an anti-mitotic drug cargo that could be activated and released within the cellular endolysosome. Therefore, when in the conjugated form the drug would be rendered non-active and therefore safe—and would only induce toxicity upon cancer cell targeting and activation.

The anti-mitotic drug: vcMMAE, valine-citrulline monomethyl auristatin E (see FIG. 2) was selected. vcMMAE consists of a lysosomally cleavable dipeptide, valine-citrulline, and the anti-mitotic agent, MMAE. Once cleaved, the MMAE drug is cytotoxic through inhibiting the polymerization of tubulin, which stops the cell from replicating.

Thus far VNP technologies have primarily focused on the delivery of drugs targeting solid tumors. As a new direction, the inventors developed soft matter nanoparticles for applications targeting lymphoma and delivering vcMMAE.

Methods

Propagation and Purification of TMV-lysine. TMV-lysine (TMV-lys) is a genetically modified TMV where reactive lysine groups were introduced on the ends of the coat proteins. Smith et al., Virology, vol. 348, no. 2, pp. 475-488 (2006). TMV-lys was propagated using *Nicotiana benthamiana* plants (a tobacco plant species). The virus was isolated via established purification procedures yielding up to 100 milligrams of TMV-lys per 100 grams of infected tobacco plant leaves. Verch et al., J. Immunol. Methods, vol. 220, no. 1-2, pp. 69-75 (1998).

UV/VIS Spectroscopy. A Thermo Scientific NanoDrop 2000 Spectrophotometer was used to measure the concentration of TMV using the TMV specific extinction coefficient ($1.36\ M^{-1}\ cm^{-1}$), the known path length ($0.1\ cm^{-1}$) and the Beer-Lambert equation. The Beer-Lambert law is defined as $A=c\varepsilon*d*c$, where c is the extinction coefficient, A is the absorbance measured at a defined wavelength, d is the path length, and c is the concentration. To solve for concentration we rearrange the equation as $A/(\varepsilon*d)$.

Chemical Conjugation. TMV-lys was reacted with 10 molar excess of N-succinmidyl-S-acetylthiopropionate (SATP) (Thermo Fisher) with 10% (v/v) dimethyl sulfide (DMSO) in 10 mM potassium phosphate buffer (pH 7.0). The resulting TMV-SATP complex was purified via ultracentrifuge, reacted with 10% deacetylation solution (v/v), (5 M Hydroxylamine, 25 mM EDTA in PBS, pH 7.4), for two hours, and then purified with a PD-10 desalting column (GE healthcare life sciences). Next, the TMV-SATP solution was reacted with 10 molar excess of vcMMAE (Med Chem Express) overnight and purified via ultracentrifuge. Yields after ultracentrifuge purification range from 70%-90%, and yields after desalting column range from 30%-50%.

SDS-PAGE. Coat proteins were analyzed using 4-12% NuPAGE gels (Invitrogen) using 1× (Nmorpholino) propanesulfonic acid (MOPS) running buffer (Invitrogen). 20 μg of protein with 4× loading LDS dye was added, and denatured through heating at 100° C. for 5 minutes. After separation, the gel was first placing the gel in destain solution (10% acetic acid, 50% methanol, and 40% $H_2O$) for 30 minutes. 10 mL of the used destain solution was then diluted with 40 mL $H_2O$ and 50 μL of Coomassie Blue R250. The gel was placed in this solution for 30 minutes to stain for protein, then immediately photographed using an AlphaImager (Biosciences) imaging system.

Transmission electron microscopy (TEM). 2 μL drops of 0.1 mg/mL TMV-vcMMAE in $H_2O$ was placed onto TEM grids and allowed to dry. The grid was then washed in DI water, and stained with 2% (w/v) uranyl acetate for two minutes. After drying, samples were examined using a Zeiss Libra 200FE transmission electron microscope operated at 200 kV.

Cell culture. Karpas 299 cells (ATCC) were maintained in RPMI-1640 at 37° C. in a 5% $CO_2$ humidified atmosphere. The medium was supplemented with 20% (v/v) heat-inactivated fetal bovine serum (FBS), and 1% (v/v) penicillin-streptomycin. All reagents were obtained from Gibco.

Cell viability assay. Cells at a concentration of 10,000 cells/mL were seeded in a sterile, tissue culture-treated, 96-well clear bottom plate for 24 hours at 37° C. in a 5% $CO_2$ humidified atmosphere. Cells were then incubated with fresh media with 0.02 nM to 200 nM VcMMAE for 72 hours. At 92 hours, Alamar Blue (ThermoFisher) was added, and cell viability was measured at 96 hours according to the manufacturer's instructions using a fluorescence plate reader with emission at 540 nM and excitation at 610 nM.

Confocal Microscopy. Karpas 299 cells were seeded at a density of 500,000 cells/well in a 96 well plate in fresh RPMI and incubated with TMV at 1,000,000 particles/cells for 8 hours at 37° C. in a 5% $CO_2$ humidified atmosphere. Cells were spun down at 500 g and washed two times with CELL buffer (0.1 mL 0.5 M EDTA, 0.5 mL fetal bovine serum, 1.25 mL 1 M HEPES pH 7.0, 48.15 mL PBS), and then fixed using 2% (v/v) paraformaldehyde in CELL buffer, then washed an additional two times in CELL buffer. Cells were washed in PB buffer (0.2% (v/v) Triton X-100 in DPBS) twice, and incubated with rabbit anti-TMV (1:500) (Pacific Immunology) and mouse anti-human LAMP-1 (1:500) (Sigma Aldrich) in CELL buffer for an hour. The cells were then washed two more times with PB buffer and spun down on cover slips at 2,000 rpm for 5 minutes. Then the cells were incubated with secondary antibodies using AlexaFluor 488-labeled goat anti-mouse antibody and AlexaFluor 555 anti-rabbit antibody (Invitrogen) in PB with 5% (v/v) goat serum for one hour. Lastly, the slips were washed two more times with CELL buffer, and then stained with DAPI (Sigma Aldrich) and imaged at 40× on an Olympus Fluo-View™ FV1000 LSCM microscope.

Results and Discussion

TMV-lys was first propagated in *N. benthamiana* plants. TMV-lys is a lysine-added mutant of TMV which displays a lysine residue instead of a serine at amino acid position 158; the amine-functional lysine group is therefore solventexposed and located at the C-terminus of the coat protein (see FIG. 1). Geiger et al., Nanoscale, vol. 5, no. 9, pp. 3808-3816 (2013) TMV-lys was extracted in yields of 1 mg of pure virus per gram of infected leaves using established virus purification techniques.

Figure 2A:
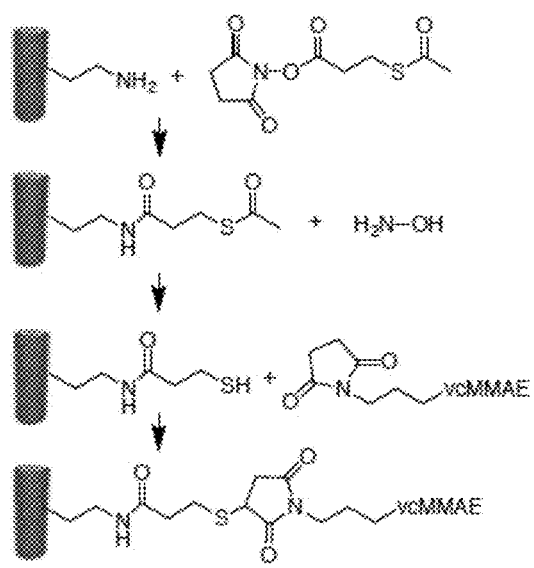
FIG. 2A and FIG. 2B provide schemes showing the chemical structures and bioconjugation reaction. A) Bioconjugation scheme steps: First TMV-lysine reacts with SATP via NHS chemistry, next TMV-SATP's thiol group is deprotected using hydroxylamine, followed by reaction of TMV-SH with the maleimide group of vcMMAE, resulting in TMV-MMAE. B) the chemical structure of vcMMAE.
Figure 2B:
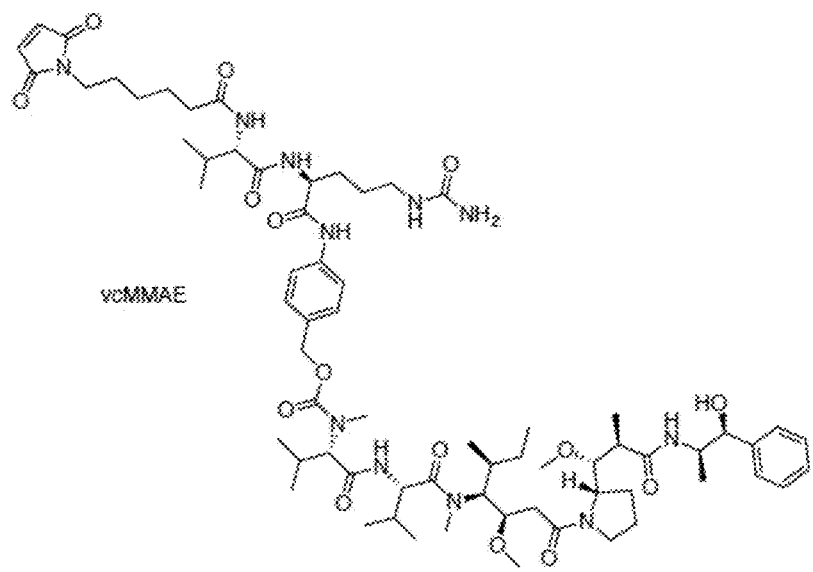

To obtain vcMMAE-loaded TMV, the anti-mitotic drug was bioconjugated using a three-step reaction (FIG. 2A). First, the amine handle of the TMV-lys was converted into a acetate-protected sulfhydryl group using the bi-functional linker N-succinimidyl-S-acetylthiopropionate (SATP), using a ratio of SATP:TMV of 15:1 (FIG. 2A). The reaction was purified via ultracentrifugation over a 40% (w-v) sucrose cushion. The TMV-SATP ending sulfhydryl group was then deprotected using hydroxylamine and purified using a PD-10 desalting column, yielding a free thiol handle for conjugation with the maleimide-terminated vcMMAE through thiol-Michael reactions; using a ratio of vcMMAE:TMV of 10:1. The structure of vcMMAE is shown in FIG. 2B. The reaction mix again was purified by ultracentrifugation over sucrose cushion and the final formulation was characterized by UV-VIS, SDS-gel, and TEM (FIGS. 3A-C).

UV/VIS spectroscopy was conducted to analyze the amount of protein recovered. Reactions starting with 5 mg of TMV-lys resulted in yields of approximately 3.7 mg of TMV-SATP, and yields of 1.3 mg of TMV-vcMMAE. This means that 75% was recovered in step 1 and only 35% of particles were recovered in step 2.

The particles were characterized after each conjugation step using SDS-PAGE (FIG. 3A). Using this technique, the TMV particle is denatured and disassembled into its coat proteins, which are analyzed by electrophoresis through a polyacrylamide matrix. Using this method, the coat proteins are separated by electrophoretic mobility based on molecular weight. Differences in the bands pattern indicate differences in the molecular weight of the various compositions of coat protein (CP) vs. CP-SATP vs. CP-vcMMAE. The band pattern reveals the molecular weight of the CPs and therefore indicates whether the drug cargo is attached.

The TMV coat protein measures 17.5-kDa and is detectable on the SDS-PAGE (Lane 1, FIG. 3A). A small percentage of coat protein dimers are also detectable at ~40-kDa molecular weight standard. The dimers are a results of inter-coat protein crosslinking based on disulfide bridges. Shifts in the band pattern indicate successful conjugation of SATP and the drug vcMMAE (FIG. 3B). The SATP linker has a molecular weight of 245.25 g/mol; a negligible shift toward higher molecular weight bands indicates successful conjugation, however, it should be noted that the SDS PAGE methods does not provide the resolution to resolve the small difference in the molecular weight change of 0.5 kDa comparing the CP vs. CP-STAP. The drug, vcMMAE, has a molecular weight of 1316.64 g/mol; a shift towards the higher molecular weight band indicates that conjugation was successful, and the CP-vcMMAE band is detectable at 20 kDa.

The SDS-gel displayed distinct bands comparing lane 1, TMV, and lane 5, TMVvcMMAE, indicating that a higher molecular weight complex was present. Densinometric analysis conducted using ImageJ showed ~100% band separation. The uniform shift of the band indicates complete conversion of the amines to thiols, followed by drug loading, i.e. the SDS-PAGE indicates that each of the 2,130 available sites were labeled with the therapeutic cargo (FIG. 3B).

Finally, transmission electron microscopy (TEM) revealed that the TMVvcMMAE formulations remained intact; imaging of negatively-stained TEM grids showed structurally sound TMV nanoparticles with dimensions of 300×18 nm (FIG. 3C). TEM images showed that the TMV rods were intact and non-aggregated after the bioconjugation and purification processes.

To conclude discussion of the synthesis of the vcMMAE-conjugated TMV; the inventors have developed a protocol allowing efficient drug loading of TMV. The chemical reaction reached completion with each of the 2,130 coat proteins being modified with a drug molecule. On a %-molecular weight basis, this translates to a drug loading efficiency of ~7% wt per TMV. This is comparable to immunotherapies which have drug loading of up to ~7% wt per IgG, and up to ~10% wt per diabody in antibody conjugated MMAE studies. Rink et al., Curr. Opin. Oncol., vol. 25, no. 6, pp. 646-651 (2013). Nevertheless, antibody-drug conjugates are limited to only carrying up to 8 drug molecules per antibody, which is far fewer than the load which TMV can carry, namely ~2,000 copies of the payload.

The inventors next set out to study the in vitro properties of the drug candidate using Karpas 299 cells, a human derived non-Hodgkin's large B cell lymphoma, and the fate of the TMV formulation in these cells, and second, drug efficacy.

A cell uptake and colocalization study was carried out to evaluate whether TMV would target and be taken up by Karpas 299 cells, and whether the particles would be targeted to the endolysosomal compartment. First, Karpas 299 cells were incubated with TMV for 8 hours using one million TMV particles per cell. Then the cells were washed to remove excess TMV, followed by staining of TMV using TMV-specific antibodies and secondary dye-labeled antibodies. At the same time, the endolyosome was stained using LAMP-1 staining. The cells were then fixed, mounted and imaged by fluorescence microscopy (FIG. 4).

Figure 4:
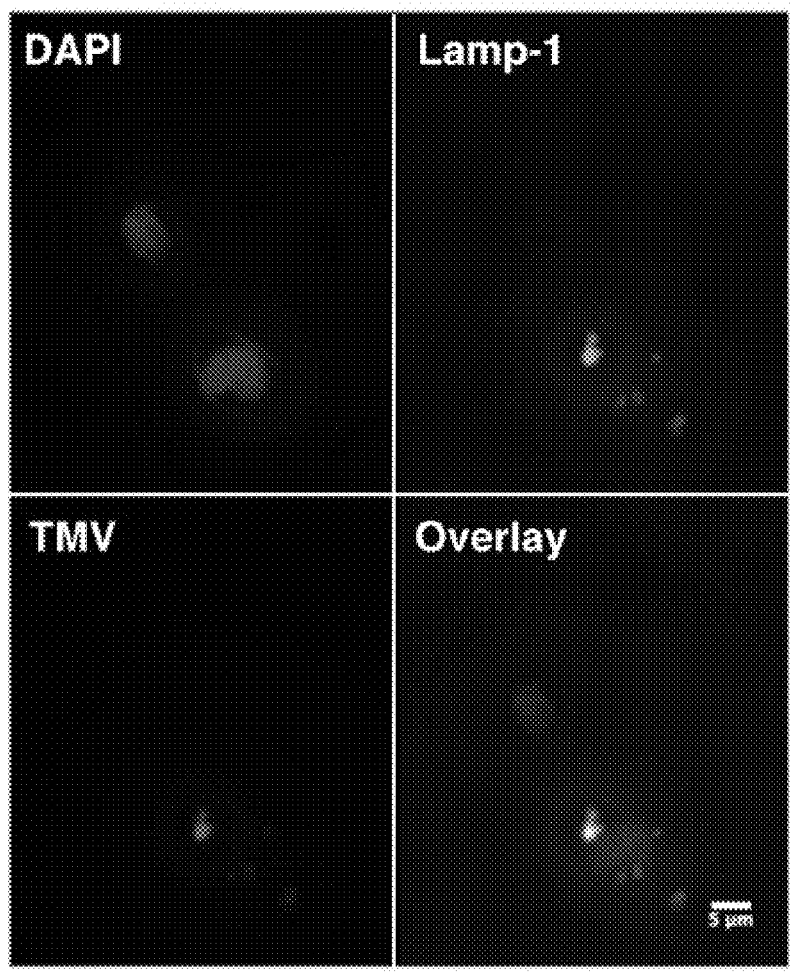
FIG. 4 provides images of Karpas 299 cell interactions with TMV. DAPI: DAPI stain showing the nuclei. Lamp1: Endolysosomes stained with mouse anti-human Lamp-1 antibody, and secondary Alexa Fluor 488 goat anti-mouse antibody. TMV: TMV particles stained with primary rabbit antibody alpha-TMV, and anti-rabbit-555. Overlay: All three labels simultaneously shown, with the colocalization of TMV and the endolysosome.

As seen in FIG. 4, the red fluorescent antibodies tagging TMV overlap with the green antibodies tagging the endolysosome. Thus the confocal microscopy imaging confirmed that the Karpas 299 cells uptake TMV, and that the nanoparticles traffic to the endolysosome. Based on these findings, I hypothesize that the TMV-vcMMAE would also be taken up by the Karpas 299 cells targeting the endolysosome. The vcMMAE drug is designed to be activated and cleaved within the endolysosomal compartment. Specifically the valine-citruline (vc)-linker is a protease-specific cleavable linker, resulting in release of the active MMAE component.

To evaluate the efficacy of TMV-vcMMAE, cell viability assays were performed using Alamar Blue assay Alamar Blue reagent is primarily made of resazurin, a nontoxic cell permeable non-fluorescent blue molecule. Upon entering viable cells, resazurin is reduced to resorufin, which is a bright red fluorescent molecule. Protocols for using the reagent are available online.

Figure 5:
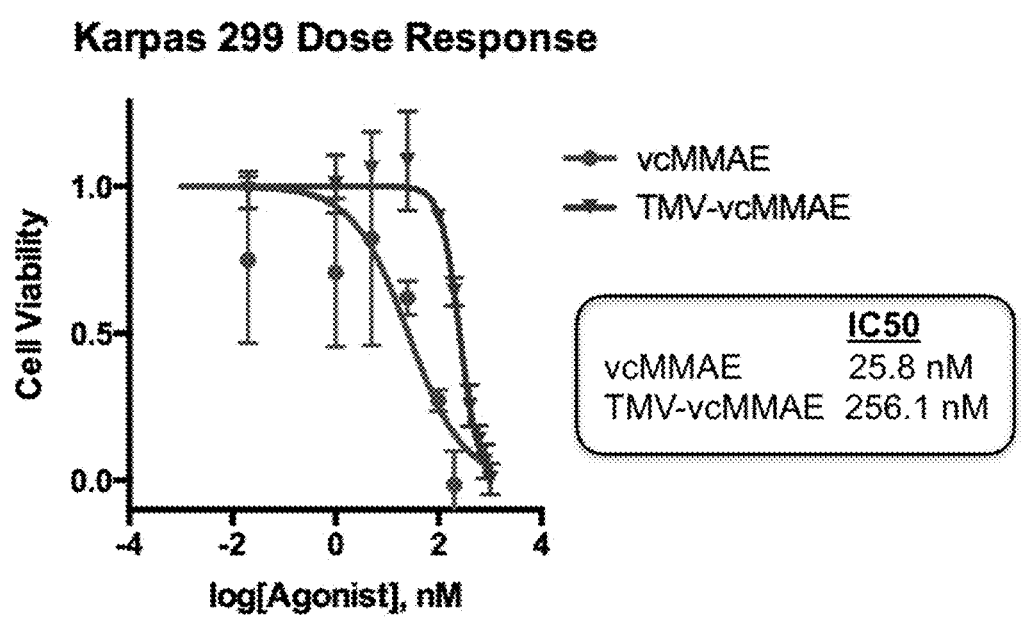
FIG. 5 provides a graph showing the results of the cell viability assay. Cell viability assay using Karpas 299 cells after treatment with vcMMAE (circles) and TMV-vcMMAE (triangles). Cell viability was determined after 72 hours using Alamar Blue assay. Error bars were calculated by standard deviation (experiments were done in triplicates). Data was analyzed and graphed using Prism® v6.0b software.

Karpas 299 cells were seeded for 24 hours and then incubated with free vcMMAE or TMV-MMAE for 72 hours. At 92 hours, Alamar Blue was added and the cells fluorescence was measured after 4 hours of incubation at 540 nm excitation and 610 nm emission. The results for both free vcMMAE and TMV-MMAE are plotted in FIG. 4, and the $IC_{50}$ values were calculated. The $IC_{50}$ value defines the drug concentration where half of the cells are killed. The $IC_{50}$ for free vcMMAE was determined to be about 25.8 nM, and the $IC_{50}$ for TMV-MMAE was found to be 256.1 nM (FIG. 5).

$IC_{50}$ values of the free vcMMAE drug vary in the literature depending on the set up of the assay, e.g. time course and cell lines used, and are found in the low nanomolar range at around 5 nM. Wen et al., Bioconjug. Chem., vol. 26, no. 1, pp. 51-62 (2015). $IC_{50}$ values of antibody drug conjugates are generally found ranging from 2 nM to 42 nM. The inventors saw a similar trend, with a low $IC_{50}$ of the free drug, and an order of magnitude higher $IC_{50}$ using VNP loaded with drug. The lower $IC_{50}$ values of the nanoparticle conjugates may be explained by lower cell uptake kinetics, as has been reported with other systems. Danhier et al., J. Controlled Release, vol. 133, no. 1, pp. 11-17 (2009); Panyam and V. Labhasetwar, Adv. Drug Deliv. Rev., vol. 55, no. 3, pp. 329-347 (2003). Nevertheless, the inventors expect that the nanoparticle-assisted targeted drug delivery approach will outperform the in vivo profiles of the free drug through enhanced biodistribution and pharmacokinetics.

CONCLUSIONS

The inventors demonstrated that TMV could be loaded with a high payload of vcMMAE, with all of its coat proteins labeled with drug for treatment of lymphoma. The particles are taken up by cancer cells and are targeted to the endo-lysosomal compartment, where the drug is then cleaved from the VNP. It was found that TMV-delivered vcMMAE was effective in killing cancer cells in vitro and demonstrated an $IC_{50}$ in the nanomolar range. The inventors found that the TMV-vcMMAE complex had a higher $IC_{50}$ value than free vcMMAE. One explanation why the efficacy of the viral nanoparticle may be lower is due to lower cell uptake kinetics.

One of the next steps for the optimization of the TMVvcMMAE therapeutic would be to give the particles further selectivity. This can be achieved through conjugation of targeting peptides or antibodies. For example, direction the drug-loaded nanoparticles with specificity for markers of diffuse large B cell lymphoma is expected to increase cell uptake rates and selectivity. CD20, CD22, and CD40 have been identified as candidate targets and nanoparticle formulations with selectivity for these targets are under development for treatment of B-cell lymphomas. Rillahan et al., Chem. Sci., vol. 5, no. 6, pp. 2398-2406 (2014); Holder et al., Eur. J. Immunol., vol. 23, no. 9, pp. 2368-2371 (1993); T. M. Allen, Nat. Rev. Cancer, vol. 2, no. 10, pp. 750-763 (2002).

Antibodies with specificity toward these markers are also in development, with some formulations already being used in the clinic for treatment of lymphoma. However, antibodies are limited in only being able to carry up to 8 drug molecules. TMV provides advantages, because this nanoparticle formulation can carry more than 2,000 drugs on its exterior. Furthermore, the interior channel can also be used for conjugation of drugs or contrast agents—toward the development of theranostics. This high number of reactive sites opens up greater flexibility compared to antibody drug conjugate therapies. Bio27 conjugation of antibodies to the TMV-vcMMAE formulation is expected to be a powerful tool for targeted drug delivery targeting Non-Hodgkin's lymphoma. In conclusion, there are many promising avenues for the further development of virus-based nanoparticle therapeutics targeting soft-cancer applications.

The complete disclosure of all patents, patent applications, and publications, and electronically available materials cited herein are incorporated by reference. The foregoing detailed description and examples have been given for clarity of understanding only. No unnecessary limitations are to be understood therefrom. In particular, the inventors are not bound by theories described herein. The invention is not limited to the exact details shown and described, for variations obvious to one skilled in the art will be included within the invention defined by the claims.

What is claimed is:

1. An anti-lymphoma virus particle, comprising a filamentous plant virus particle linked to an antimitotic agent, wherein the filamentous plant virus particle is a member of the Alphaflexiviridae family.

2. The anti-lymphoma virus particle of claim 1, wherein the exterior surface of the plant virus particle has been PEGylated.

3. The anti-lymphoma virus particle of claim 1, wherein the antimitotic agent is a dolastatin.

4. The anti-lymphoma virus particle of claim 3, wherein the dolastatin is monomethyl auristatin E (MMAE).

5. The anti-lymphoma virus particle of claim 3, wherein the dolastatin is valine-citrulline monomethyl auristatin E (vcMMAE).

6. The anti-lymphoma virus particle of claim 1, wherein the antimitotic agent is covalently conjugated to the exterior of the plant virus particle.

7. The anti-lymphoma virus particle of claim 1, wherein a targeting ligand is attached to the exterior of the plant virus particle.

8. The anti-lymphoma virus particle of claim 1, wherein the filamentous plant virus particle is Potato Virus X.

9. The anti-lymphoma virus particle of claim 8, wherein the anti-mitotic agent is valine-citrulline monomethyl auristatin E (vcMMAE).

10. A method of treating lymphoma in a subject in need thereof, the method comprising administering to the subject a therapeutically effective amount of an anti-lymphoma virus particle, the anti-lymphoma virus particle comprising a filamentous plant virus particle linked to an antimitotic agent, wherein the filamentous plant virus particle is a member of the Alphaflexiviridae family.

11. The method of claim 10, wherein the lymphoma is non-Hodgkin's lymphoma.

12. The method of claim 10, wherein the anti-lymphoma virus particle is administered together with a pharmaceutically acceptable carrier.

13. The method of claim 10, wherein the antimitotic agent is a dolastatin.

14. The method of claim 13, wherein the dolastatin is MMAE.

15. The method of claim 13, wherein the dolastatin is vcMMAE.

16. The method of claim 10, wherein the antimitotic agent is covalently conjugated to the exterior of the plant virus particle.

17. The method of claim 10, wherein a targeting ligand is attached to the exterior of the plant virus particle.

18. The method of claim 10, wherein the filamentous plant virus particle is Potato Virus X.

19. The method of claim 18, wherein the anti-mitotic agent is valine-citrulline monomethyl auristatin E (vcMMAE).

* * * * *